United States Patent [19]

Assmann et al.

[11] Patent Number: 6,034,116
[45] Date of Patent: Mar. 7, 2000

[54] MIXTURES OF SUBSTITUTED BENZIMIDAZOLES WITH POLYETHER ANTIBIOTICS OR SYNTHETIC COCCIDIOSTATS AS AGENTS FOR USE AGAINST PARASITIC PROTOZOA

[75] Inventors: Lutz Assmann, Eutin; Bernd Baasner, Bergisch Gladbach; Axel Haberkorn, Wuppertal; Folker Lieb, Leverkusen; Winfried Lunkenheimer, Wuppertal; Norbert Lui, Köln, all of Germany

[73] Assignee: Bayer Aktiengesellschaft, Leverkusen, Germany

[21] Appl. No.: 08/952,758

[22] PCT Filed: May 20, 1996

[86] PCT No.: PCT/EP96/02164

§ 371 Date: Nov. 19, 1997

§ 102(e) Date: Nov. 19, 1997

[87] PCT Pub. No.: WO96/38140

PCT Pub. Date: Dec. 5, 1996

[30] Foreign Application Priority Data

May 31, 1995 [DE] Germany .......................... 195 19 821

[51] Int. Cl.$^7$ .................................................. A61K 31/415
[52] U.S. Cl. .......................... 514/394; 514/395; 514/629
[58] Field of Search ...................... 514/394, 395, 514/629

[56] References Cited

U.S. PATENT DOCUMENTS 5,331,003  7/1994  O'Doherty .............................. 514/394
5,482,956  1/1996  Lunkenheimer .

FOREIGN PATENT DOCUMENTS 4237617  11/1994  Germany .

*Primary Examiner*—Rebecca Cook
*Attorney, Agent, or Firm*—Joseph C. Gil; Godfried R. Akorli

[57] ABSTRACT

The present invention relates to mixtures of substituted benzimidazoles and polyether antibiotics or synthetically prepared coccidiostats for controlling parasitic protozoa in livestock.

3 Claims, No Drawings

MIXTURES OF SUBSTITUTED BENZIMIDAZOLES WITH POLYETHER ANTIBIOTICS OR SYNTHETIC COCCIDIOSTATS AS AGENTS FOR USE AGAINST PARASITIC PROTOZOA

This is a 371 of PCT/EP96/02164 filed May 30, 1996.

The present invention relates to mixtures of substituted benzimidazoles with a polyether antibiotic or a synthetically prepared coccidiostat as compositions to control parasitic protozoa and, in particular, coccidia, and fish parasites and insect parasites.

Substituted benzimidazoles and their use as insecticides, fungicides and herbicides have already been disclosed (EP-OS (European Published Specifications) 87 375, 152 360, 181 826, 239 508, 260 744, 266 984, U.S. Pat. Nos. 3,418,318, 3,472,865, 3,576,818, 3,728,994).

Halogenated benzimidazoles and their effect as anthelmintics, coccidiostats and pesticides have been disclosed (DE-OS (German Published Specification) 2 047 369, DE-OS (German Published Specification) 4 237 617). Mixtures of nitro-substituted benzimidazoles and polyether antibiotics have been disclosed as coccidiostats (U.S. Pat. No. 5,331,003). Their effect is as yet unsatisfactory in all cases.

Coccidiosis is a disease caused by single-cell parasites (protozoa). It may cause great losses in particular in poultry rearing. In order to avoid this, the stocks are treated prophylactically with coccidiostats. The development of resistance to the compositions used results after only a relatively few years in serious problems. On the other hand, it is possible by using chemically completely new coccidiostats, in particular combinations, to control even polyresistant parasite strains.

The present invention relates to mixtures of substituted benzimidazoles of the formula (I)

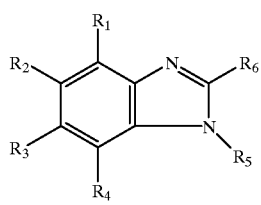

(I)

in which
  $R_1$, $R_2$, $R_3$ and R4 each, independently of one another, represent hydrogen, halogen, represent in each case optionally substituted alkyl, alkoxy, alkylthio, alkylsulphinyl, alkylsulphonyl, represent optionally substituted fused-on dioxyalkylene, but where at least one of the substituents $R_1$, $R_2$, $R_3$ and $R_4$ is different from hydrogen and halogen,
  $R_5$ represents hydrogen, represents alkyl which is substituted one or more times, identically or differently, by OH, CN, $NH_2$, alkyl, cycloalkyl, alkenyl, alkinyl, alkoxy, halogenoalkoxy, alkylthio, halogenoalkylthio, alkenoxy, alkinoxy, aminocarbonyl, optionally substituted alkylcarbonyl, optionally substituted (het-)arylcarbonyl, optionally substituted alkoxycarbonyl (AlkO—CO—), optionally substituted alkoxycarbonyloxy (AlkOCOO—), aminosulphonyl ($SO_2NH_2$), optionally substituted mono- or dialkylaminosulphonyl, acylated amino (AlkCON($R_7$)— or AlkOCON($R_7$)—), where $R_7$ is equal to hydrogen, alkyl or cycloalkyl, or optionally substituted alkylsulphonylamino (AlkylSO$_2$NH—), or alkylsulphonyl-N-alkylamino (ArylSO$_2$NAlkyl—), optionally substituted arylsulphonylamino (ArylSO$_2$NH—) or arylsulphonyl-N-alkylamino (ArylSO$_2$NAlk—) optionally substituted dialkylamino, furthermore $R_5$ represents optionally substituted alkoxycarbonyl, optionally substituted (het-)aryloxycarbonyl. alkylsulphonyl, alkenylsulphonyl, (het-)arylsulphonyl, or —SO$_2$NR$_8$R$_9$, —CONR$_8$R$_9$ or —P(O)(NR$_8$R$_9$)$_2$, where $R_8$ and $R_9$ represent H or alkyl which is optionally substituted by one or more radicals, R6 represents fluoroalkyl, with one or more of the following compounds:

Polyether antibiotics such as maduramycin, lasalocid, monensin, narasin, salinomycin or synthetic coccidiostats such as

| | |
|---|---|
| 1(-(4-Amino-2-n-propyl-5-pyrimidinylmethyl)-2-picolinium chloride | Amprolium |
| 1(-(4-Amino-2-n-propyl-5-pyrimidinylmethyl)-2-picolinium chloride + sulfaquinoxaline | Amprolium + sulfaquinoxaline |
| 1(-(4-Amino-2-n-propyl-5-pyrimidinylmethyl)-2-picolinium chloride + sulfaquinoxaline + ethopabate | Amprolium + sulfaquinoxaline + ethopabate |
| 4,4-Dinitrocarbanilide + 2-hydroxy-4,6-dimethyl-pyrimidine | Nicarbazin |
| 3,5-Dichloro-2,6-dimethyl-4-pyridinol | Clopidol |
| 3,5-Dichloro-2,6-dimethyl-4-pyridinol + methyl 7-benzyloxy-6-butyl-1,4-dihydro-4-oxylquinoline-3-carboxylate | Clopidol + methylbenzoquate |
| Ethyl 6-n-decyloxy-7-ethoxy-4-hydroxyquinoline-3-carboxylate | Decoquinate |
| 9-(2-Chloro-6-fluorophenylmethyl)-9H-purin-6-amine | Arprinocid |
| (±)-2,6-Dichloro-alpha-(4-chlorophenyl)-4-(4,5-dihydro-3,5-dioxo-1,2,4-triazin-2(3H)-yl)-benzene-acetonitrile | Benzeneacetonitrile, diclazuril |
| 1-[3-Methyl-4-(4'-trifluoromethylthiophenoxy)-phenyl]-3-methyl-1,3,5-triazine-2,4,6(1H, 3H, 5H)-trione | Toltrazuril |
| 4,4-Dinitrocarbanilide + 2-hydroxy-4,6-dimethyl-pyrimidine [= nicarbazin] | Robenidine |
| 7-Bromo-6-chloro-febrifugin | Halofuginone |
| 3,5-Dinitro-o-toluamide | Zoalene | as compositions for controlling parasitic protozoa, in particular coccidia, in livestock.

The benzimidazoles which can be used according to the invention are known. They are generally defined by the formula (I). Preferred compounds of the formula (I) are those in which $R_1$, $R_2$, $R_3$ and $R_4$ each, independently of one another, represent hydrogen, fluorine, chlorine, bromine, iodine, represent in each case straight-chain or branched alkyl, alkoxy, alkylthio, alkylsulphinyl, alkylsulphonyl with in each case 1 to 8 carbon atoms, represent cycloalkyl with 3 to 8 carbon atoms, represent in each case straight-chain or branched halogenoalkyl, halogenoalkoxy, halogenoalkylthio, halogenoalkylsulphinyl, halogenoalkylsulphonyl with in each case 1 to 6 carbon atoms and 1 to 13 identical or different halogen atoms or represent optionally singly or multiply, identically or differently by 1 to 10 halogens and/or straight-chain or branched alkyl with 1 to 4 carbon atoms and/or straight-chain or branched halogenoalkyl with 1 to 4 carbon atoms and 1 to 9 halogen atoms doubly linked dioxyalkylene with 1 to 5 carbon atoms, but where at least one of the substituents $R_1$, $R_2$, $R_3$ and $R_4$ is different from hydrogen and halogen, $R_5$ represents hydrogen, represents alkyl with 1 to 4 carbon atoms, which is substituted one or more times, identically or differently, by OH, CN, $NH_2$, alkyl with 1 to 4 carbon atoms, cycloalkyl with 3 to 10 carbon atoms, alkenyl with 2 to 6 carbon atoms, alkinyl with 2 to 6 carbon atoms, alkyloxy with 1 to 6 carbon atoms, halogenoalkoxy with 1 to 6 carbon atoms and 1 to 5 halogens, alkylthio with 1 to 6 carbon atoms, halogenoalkylthio with 1 to 6 carbon atoms and 1 to 5 halogens, alkenyloxy with 2 to 6 carbon atoms, alkinyloxy with 3 to 6 carbon atoms, optionally substituted alkylcarbonyl with 1 to 6 carbon atoms, optionally substituted phenyl- or hetarylcarbonyl, optionally substituted alkoxycarbonyl with 1 to 6 carbon atoms, optionally substituted alkoxycarbonyloxy with 1 to 6 carbon atoms, aminosulphonyl ($NH_2SO_2$—), optionally substituted mono- or dialkylamninosulphonyl with 1 to 6 carbon atoms, acylated amino (AlkOCON($R_7$)— or (AlkCON($R_7$)—) where $R_7$ is equal to hydrogen or alkyl with 1 to 6 carbon atoms or cycloalkyl with 3 to 8 carbon atoms, with 1 to 6 carbon atoms, optionally substituted alkylsulphonylamino with 1 to 6 carbon atoms, optionally substituted alkylsulphonyl-N-alkylamino with 1 to 6 carbon atoms, optionally substituted phenylsulphonylamino, optionally substituted phenylsulphonyl-N-alkylamino with 1 to 6 carbon atoms, optionally substituted dialkylamino with 1 to 8 carbon atoms, furthermore $R_5$ represents the optionally substituted radicals alkyloxycarbonyl with 1 to 6 carbon atoms, alkylsulphonyl or alkenylsulphonyl with 1 to 6 carbon atoms, which are optionally substituted by 1 to 13 halogen atoms, optionally substituted phenylsulphonyl, optionally substituted heteroarylsulphonyl, phenoxycarbonyl, or —$SO_2NR_8R_9$, —$CONR_8R_9$ or —$P(O)NR_8R_9)_2$, where $R_8$ and $R_9$ represent hydrogen or an alkyl with 1 to 4 carbon atoms, which are optionally substituted by one of the radicals mentioned above for $R_5$, Substituents of the optionally substituted radicals which may be mentioned are the following substituents:

Halogen, OH, $NH_2$, alkylamino with 1 to 6 carbon atoms, cyano, nitro, $CO_2H$, in each case straight-chain or branched alkyl, alkoxy, alkylthio, alkylsulphinyl or alkylsulphonyl with in each case 1 to 6 carbon atoms, in each case straight-chain or branched halogenoalkyl, halogenoalkoxy, halogenoalkylthio, halogenoalkylsulphinyl or halogenoalkylsulphonyl with, in each case, 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl with, in each case, 1 to 6 carbon atoms in the individual alkyl moieties, doubly linked dioxyalkylene which is optionally substituted 1 to 6 times, identically or differently, by halogen and/or straight-chain or branched alkyl with 1 to 6 carbon atoms and/or straight-chain or branched halogenoalkyl with 1 to 6 carbon atoms and 1 to 13 identical or different halogen atoms and has 1 to 6 carbon atoms, or phenyl or phenoxy which is optionally substituted one to five times, identically or differently, by halogen and/or straight-chain or branched alkyl with 1 to 4 carbon atoms and 1 to 9 identical or different halogen atoms, each of which in turn can carry the abovementioned radicals.

Acyl radicals of the listed radicals which may be mentioned are the radicals alkoxycarbonyl with 1 to 6 carbon atoms, alkylcarbonyl with 1 to 6 carbon atoms, alkoxycarbonyloxy with 1 to 6 carbon atoms, alkylsulphonyl with 1 to 6 carbon atoms, benzoyl, which is optionally substituted by one of the abovementioned radicals, alkenylcarbonyl with 2 to 6 carbon atoms.

$R_6$ represents 1 to 15 fluoro-$C_1$–$C_7$-alkyl.

The substituents in compounds of the formula (I) particularly preferably have the following meaning:

$R_1$, $R_2$, $R_3$ and $R_4$ in each case, independently of one another, represent hydrogen, fluorine, chlorine or bromine, represent in each case straight-chain or branched alkyl, alkoxy, alkylthio, alkylsulphinyl, alkylsulphonyl with, in each case, 1 to 4 carbon atoms, represent cycloalkyl with 3 to 6 carbon atoms, represent in each case straight-chain or branched halogenoalkyl, halogenoalkoxy, halogenoalkylthio, halogenoalkylsulphinyl, halogenoalkylsulphonyl with, in each case, 1 to 4 carbon atoms and 1 to 9 identical or different halogen atoms, in particular fluorine and chlorine atoms or represent optionally singly or multiply, identically or differently, by 1 to 6 halogens, in particular fluorine and chlorine atoms and/or straight-chain or branched alkyl with 1 to 4 carbon atoms and/or straight-chain or branched halogenoalkyl with 1 to 4 carbon atoms and 1 to 6 halogen atoms doubly linked dioxyalkylene with 1 to 3 carbon atoms, but where at least one of the substituents $R_1$, $R_2$, $R_3$ and $R_4$ is different from hydrogen and halogen, $R_5$ represents hydrogen, represents alkyl with 1 to 3 carbon atoms, in particular represents methyl and ethyl, which is substituted by OH, CN, $NH_2$, alkyl, with 1 to 4 carbon atoms, in particular methyl or ethyl, alkenyl with 2 to 4 carbon atoms, alkinyl with 2 to 4 carbon atoms, alkyloxy with 1 to 4 carbon atoms, in particular alkoxy such as methoxy, ethoxy, propoxy, i-propoxy, halogenoalkoxy with 1 to 4 carbon atoms and 1 to 5 halogen atoms, in particular trifluoromethoxy, pentafluoroethoxy, fluoropropoxy, alkylthio with 1 to 4 carbon atoms, halogenoalkylthio with 1 to 4 carbon atoms and 1 to 5 halogens, alkenyloxy with 2 to 4 carbon atoms, alkinyloxy with 3 to 4 carbon atoms, optionally substituted alkylcarbonyl with 1 to 4 carbon atoms, optionally substituted phenylcarbonyl, optionally substituted alkoxycarbonyl with 1 to 4 carbon atoms, in particular alkoxycarbonyls such as methoxycarbonyl, ethoxycarbonyl, propoxycarbonyl, i-propoxycarbonyl, t-butoxycarbonyl, optionally substituted alkoxycarbonyloxy with 1 to 4 carbon atoms, aminosulphonyl ($NH_2SO_2$—), optionally substituted mono- or dialkylaminosulphonyl with 1 to 4 carbon atoms, acylated amino with 1 to 6 carbon atoms, where $R_7$ is equal to hydrogen or alkyl with 1 to 4 carbon atoms or cycloalkyl with 3 to 6 carbon atoms, optionally substituted alkylsulphonylamino with 1 to 4 carbon atoms, optionally substituted alkylsulphonyl-N-alkylamino with 1 to 4 carbon atoms, optionally substituted phenylsulphonylamino, optionally substituted phenylsulphonyl-N-alkylamino with 1 to 4 carbon atoms, optionally substituted dialkylamino with 1 to 4 carbon atoms, furthermore $R_5$ represents the optionally substituted radicals alkyloxycarbonyl with 1 to 4 carbon atoms, alkylsulphonyl or alkenylsulphonyl with 1 to 4 carbon atoms, which are optionally substituted with 1 to 9 halogens, optionally substituted phenylsulphonyl, heteroarylsulphonyl, where heteroaryl represents a 5 or 6-membered heterocycle which is optionally substituted by alkyl with 1 to 4 carbon atoms or halogen or by a substituent listed under $R_5$, or phenoxycarbonyl, or $SO_2NR_8R_9$, $CONR_8R_9$ or —$P(O)(NR_8R_9)_2$, where $R_8$ and $R_9$ represent hydrogen or an alkyl with 1 to 4 carbon atoms, which are optionally substituted by one of the radicals mentioned above for $R_5$.

Substituents of the optionally substituted radicals which may be mentioned are the following substituents:

Halogen, in particular fluorine or chlorine, OH, $NH_2$, alkylamino with 1 to 4 carbon atoms, in particular methylamino, ethylamino, dimethylamino, diethylamino bis-(trifluoromethylamino), cyano, nitro, $CO_2H$, in each case straight-chain or branched alkyl, alkoxy, alkylthio, alkylsulphinyl or alkylsulphonyl with, in each case, 1 to 4 carbon atoms, in particular methyl, ethyl, methoxy, ethoxy or methylmercapto, in each case straight-chain or branched halogenoalkyl, halogenoalkoxy, halogenoalkylthio, halogenoalkylsulphinyl or halogenoalkylsulphonyl with, in each case, 1 to 4 carbon atoms and 1 to 9 identical or different halogen atoms, in particular trifluoromethyl, pentafluoroethyl, fluorochloroethyl, trichloroethyl, trifluoromethoxy, trichloromethoxy, trifluoromethylmercapto, in each case straight-chain or branched alkoxyalkyl, alkoxyalkoxy, in particular methoxyethoxy, ethoxyethoxy, ethoxyethyl, alkanoyl, alkoxycarbonyl or alkoxyiminoalkyl with, in each case, 1 to 4 carbon atoms in the individual alkyl moieties, in particular acetyl, phenyl or phenoxy which is optionally substituted one to five times, identically or differently, by halogen and/or straight-chain or branched alkyl with 1 to 4 carbon atoms and 1 to 9 identical or different halogen atoms, in particular phenyl or phenoxy, each of which in turn can carry the abovementioned radicals.

$R_6$ represents 1 to 7 fluoro-$C_1$–$C_3$-alkyl.

Very particularly preferred compounds of the formula (I) are those in which the radicals have the following meaning:

$R_1$, $R_2$, $R_3$ and $R_4$ represent hydrogen, halogen, in particular chlorine or bromine, represent in each case straight-chain or branched alkyl, alkoxy, alkylthio, alkylsulphinyl, alkylsulphonyl with, in each case 1 to 4 carbon atoms, in particular methyl, methoxy, methylthio, methylsulphinyl or methylsulphonyl, represent in each case straight-chain or branched halogenoalkyl, halogenoalkoxy, halogenoalkylthio, halogenoalkylsulphinyl, halogenoalkylsulphonyl with, in each case, 1 to 4 carbon atoms and 1 to 9 identical or different fluorine or chlorine atoms, in particular for trifluoromethyl, trifluoromethoxy, trifluoromethylthio, trifluoromethylsulphinyl, trifluoromethylsulphonyl, represent doubly linked dioxyalkylene which is optionally substituted optionally by fluorine and/or chlorine atoms and has 1 to 2 carbon atoms, in particular represent $OCH_2O$, $OCH_2CH_2O$, $OCF_2CF_2O$, $OCF_2O$, $OCClFCClFO$, $R_5$ represents hydrogen, represents methyl or ethyl which are substituted by CN, by alkyl with 1 to 4 carbon atoms, in particular methyl, alkenyl with 2 to 4 carbon atoms, in particular —$CH=CH_2$ or —$CH=CHMe$, alkinyl with 2 to 4 carbon atoms, in particular —CCH or —CCMe, by alkoxy with 1 to 4 carbon atoms, in particular alkoxy such as methoxy, ethoxy, propoxy, i-propoxy, by alkinyloxy with 3 to 4 carbon atoms, in particular —$OCH_2CCH$ or —$OCH_2CCMe$, by alkylcarbonyl with 1 to 4 carbon atoms, in particular acetyl, propionyl, i-propionyl or t-butionyl, by optionally substituted phenylcarbonyl, in particular benzoyl, by optionally substituted alkoxycarbonyl with 1 to 4 carbon atoms, in particular —$CO_2Me$, —$CO_2Et$, —$CO_2Pr$, —$CO_2i$-Pr or —$CO_2tBu$, by acylated amino with 1 to 6 carbon atoms, where $R_7$ is equal to hydrogen or alkyl with 1 to 4 carbon atoms or cycloalkyl with 3 to 6 carbon atoms, in particular —$N(Me)CO_2Me$, —$N(Me)CO_2Et$, —$N(Et)CO_2Et$, —$N(Et)CO_2Me$, —$N(Pr)CO_2Et$, —$N(Bu)CO_2Me$, —$N(t$-$Bu)CO_2Me$, —$N(Bu)CO_2Et$, —$N(C_6H_{11})CO_2Et$, —NHCOMe, —NHCOEt or —NHCOPr, by optionally substituted alkylsulphonylamino with 1 to 4 carbon atoms, optionally substituted alkylsulphonyl-N-alkylamino, in particular —$NMeSO_2Me$, —$NEtSO_2Et$, $NMeSO_2Et$, —$NEtSO_2Me$, optionally substituted phenylsulphonylamino, optionally substituted phenylsulphonyl-N-alkylamino with 1 to 4 carbon atoms, in particular —$NMeSO_2Ph$, —$NEtSO_2Ph$. $R_5$ furthermore represents the optionally substituted radicals of alkyloxycarbonyl with 1 to 4 carbon atoms, alkylsulphonyl or alkenylsulphonyl with 1 to 4 carbon atoms, in particular $MeSO_2$—, $EtSO_2$—, $PrSO_2$— or $CH_2=CMeCH_2SO_2$—, optionally substituted phenylsulphonyl, in particular phenylsulphonyl or 2.4.6trimethyl-phenylsulphonyl, optionally substituted heteroarylsulphonyl, where heteroaryl represents a 5 or 6-membered heterocycle which is substituted by fluorine, chlorine or bromine and/or is substituted by an alkyl with 1 to 4 carbon atoms, in particular methyl and/or by a substituent mentioned under $R_5$, in particular $MeO_2C$ and contains one to three identical or different heteroatoms, in particular nitrogen, sulphur and/or oxygen, phenoxycarbonyl, or —$SO_2NR_8R_9$, —$CONR_8R_9$ or —$PO(NR_8R_9)_2$, where $R_8$ and $R_9$ represent hydrogen or an alkyl with 1 to 4 carbon atoms, which are optionally substituted by one of the radicals mentioned above for $R_5$, in particular represent —$SO_2NMe_2$ or —$SO_2NEt_2$, $PO(NMe_2)_2$, $CONMe_2$ or $CONiPr_2$, $R_6$ represents $CF_3$, $CHF_2$ or $C_2F_5$.

The following substituted benzimidazoles of the general formula (I) may be specifically mentioned:

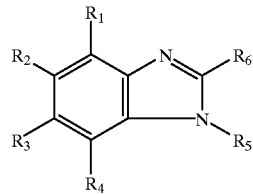

(I)

| No. | $R_1$ | $R_2$ | $R_3$ | $R_4$ | $R_5$ | $R_6$ |
|---|---|---|---|---|---|---|
| 1 | H | Br | $CF_3$ | H | H | $CF_3$ |
| 2 | H | Br | $CF_3$ | H | $CH_2CN$ | $CF_3$ |
| 3 | H | $CF_3$ | Br | H | $CH_2CN$ | $CF_3$ |
| 4 | H | Br | $CF_3$ | H | $CH_2OEt$ | $CF_3$ |
| 5 | H | $CF_3$ | Br | H | $CH_2OEt$ | $CF_3$ |
| 6 | H | Br | $CF_3$ | H | $CH_2OiPr$ | $CF_3$ |
| 7 | H | $CF_3$ | Br | H | $CH_2OiPr$ | $CF_3$ |
| 8 | H | Br | $CF_3$ | H | $CH_2COMe$ | $CF_3$ |
| 9 | H | $CF_3$ | Br | H | $CH_2COMe$ | $CF_3$ |
| 10 | H | Br | $CF_3$ | H | $CH_2OCH(CH_2F)_2$ | $CF_3$ |
| 11 | H | $CF_3$ | Br | H | $CH_2OCH(CH_2F)_2$ | $CF_3$ |
| 12 | H | Br | $CF_3$ | H | $CH_2N(Me)CO_2Me$ | $CF_3$ |
| 13 | H | $CF_3$ | Br | H | $CH_2N(Me)CO_2Me$ | $CF_3$ |
| 14 | H | Br | $CF_3$ | H | $CH_2N(Bu)CO_2Et$ | $CF_3$ |
| 15 | H | $CF_3$ | Br | H | $CH_2N(Bu)CO_2Et$ | $CF_3$ |
| 16 | H | Br | $CF_3$ | H | $CH_2N(t-Bu)CO_2Et$ | $CF_3$ |
| 17 | H | $CF_3$ | Br | H | $CH_2N(t-Bu)CO_2Et$ | $CF_3$ |
| 18 | H | Br | $CF_3$ | H | $CH_2N(C_6H_{11})-CO_2Et$ | $CF_3$ |
| 19 | H | $CF_3$ | Br | H | $CH_2N(C_6H_{11})-CO_2Et$ | $CF_3$ |
| 20 | H | Cl | $CF_3$ | H | H | $CF_3$ |
| 21 | H | Cl | $CF_3$ | H | $CH_2CN$ | $CF_3$ |
| 22 | H | $CF_3$ | Cl | H | $CH_2CN$ | $CF_3$ |
| 23 | H | Cl | $CF_3$ | H | $CH_2OEt$ | $CF_3$ |
| 24 | H | $CF_3$ | Cl | H | $CH_2OEt$ | $CF_3$ |
| 25 | H | Cl | $CF_3$ | H | $CH_2COMe$ | $CF_3$ |
| 26 | H | $CF_3$ | Cl | H | $CH_2COMe$ | $CF_3$ |
| 27 | H | Cl | $CF_3$ | H | $CH(Me)COMe$ | $CF_3$ |
| 28 | H | $CF_3$ | Cl | H | $CH(Me)COMe$ | $CF_3$ |
| 29 | H | Cl | $CF_3$ | H | $CH_2COtBu$ | $CF_3$ |
| 30 | H | $CF_3$ | Cl | H | $CH_2COtBu$ | $CF_3$ |
| 31 | H | Cl | $CF_3$ | H | $CH_2COPh$ | $CF_3$ |
| 32 | H | $CF_3$ | Cl | H | $CH_2COPh$ | $CF_3$ |
| 33 | H | Cl | $CF_3$ | H | $CH_2CCH$ | $CF_3$ |
| 34 | H | $CF_3$ | Cl | H | $CH_2CCH$ | $CF_3$ |
| 35 | H | Cl | $CF_3$ | H | $CH_2NHCOMe$ | $CF_3$ |
| 36 | H | $CF_3$ | Cl | H | $CH_2NHCOMe$ | $CF_3$ |
| 37 | H | Cl | $CF_3$ | H | $CH_2N(tBu)CO_2Me$ | $CF_3$ |
| 38 | H | $CF_3$ | Cl | H | $CH_2N(tBu)CO_2Me$ | $CF_3$ |
| 39 | H | Cl | $CF_3$ | H | $CH_2N(Me)CO_2Me$ | $CF_3$ |
| 40 | H | $CF_3$ | Cl | H | $CH_2N(Me)CO_2Me$ | $CF_3$ |
| 41 | H | $CF_3$ | Cl | H | $CH_2N(Et)CO_2Me$ | $CF_3$ |
| 42 | H | Cl | $CF_3$ | H | $CH_2N(Et)CO_2Me$ | $CF_3$ |
| 43 | H | $CF_3$ | Cl | H | $CH_2N(Me)SO_2Ph$ | $CF_3$ |
| 44 | H | Cl | $CF_3$ | H | $CH_2N(Me)SO_2Ph$ | $CF_3$ |
| 45 | H | $CF_3$ | Cl | H | $CH_2N(Me)SO_2Me$ | $CF_3$ |
| 46 | H | Cl | $CF_3$ | H | $CH_2N(Me)SO_2Me$ | $CF_3$ |
| 47 | H | $SOCF_3$ | Cl | H | H | $CF_3$ |
| 48 | H | $SO_2CF_3$ | Cl | H | H | $CF_3$ |
| 49 | H | $OCF_3$ | Cl | H | H | $CF_3$ |
| 50 | H | $OCF_3$ | Cl | H | $CH_2N(Bu)CO_2Et$ | $CF_3$ |
| 51 | H | Cl | $OCF_3$ | H | $CH_2N(Bu)CO_2Et$ | $CF_3$ |
| 52 | H | $OCF_3$ | Cl | H | $CH_2N(Pr)CO_2Et$ | $CF_3$ |
| 53 | H | Cl | $OCF_3$ | H | $CH_2N(Pr)CO_2Et$ | $CF_3$ |
| 54 | H | $OCF_3$ | Cl | H | $CH_2N(Me)CO_2Me$ | $CF_3$ |
| 55 | H | Cl | $OCF_3$ | H | $CH_2N(Me)CO_2Me$ | $CF_3$ |
| 56 | H | $OCF_3$ | Cl | H | $CH_2CN$ | $CF_3$ |
| 57 | H | Cl | $OCF_3$ | H | $CH_2CN$ | $CF_3$ |
| 58 | H | Br | $OCF_3$ | H | H | $CF_3$ |
| 59 | H | Br | $OCF_3$ | H | $CH_2CN$ | $CF_3$ |
| 60 | H | $OCF_3$ | Br | H | $CH_2CN$ | $CF_3$ |
| 61 | H | Br | $OCF_3$ | H | $CH_2OEt$ | $CF_3$ |
| 62 | H | $OCF_3$ | Br | H | $CH_2OEt$ | $CF_3$ |
| 63 | H | $OCF_3$ | Br | H | $SO_2NMe_2$ | $CF_3$ |
| 64 | H | Br | $OCF_3$ | H | $CH_2N(Me)CO_2Me$ | $CF_3$ |
| 65 | H | $OCF_3$ | Br | H | $CH_2N(Me)CO_2Me$ | $CF_3$ |

-continued

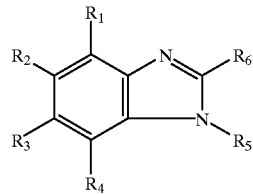

(I)

| No. | R₁ | R₂ | R₃ | R₄ | R₅ | R₆ |
|---|---|---|---|---|---|---|
| 66 | H | Br | OCF₃ | H | CH₂N(Et)CO₂Et | CF₃ |
| 67 | H | OCF₃ | Br | H | CH₂N(Et)CO₂Et | CF₃ |
| 68 | H | Br | OCF₃ | H | CH₂N(Me)CO₂Et | CF₃ |
| 69 | H | CF₃O | OCH₃ | H | H | CF₃ |
| 70 | H | CF₃ | OCH₃ | H | H | CF₃ |
| 71 | H | OCF₃ | OCF₃ | H | SO₂NMe₂ | CF₃ |
| 72 | H | CF₃O | OCF₃ | H | CH₂OCH₂CCH | CF₃ |
| 73 | H | OCF₂O | | H | H | CF₃ |
| 74 | H | OCF₂CF₂O | | H | H | CF₃ |
| 75 | H | OCF₂CF₂O | | H | H | CHF₂ |
| 76 | H | OCF₂CF₂O | | H | H | C₂F₅ |
| 77 | H | OCF₂CF₂O | | H | CH₂CN | CF₃ |
| 78 | H | OCF₂CF₂O | | H | CH₂OEt | CF₃ |
| 79 | H | OCF₂CF₂O | | H | CH₂OiPr | CF₃ |
| 80 | H | OCF₂CF₂O | | H | CH₂N(Me)CO₂Et | CF₃ |
| 81 | H | OCF₂CF₂O | | H | CH₂N(Me)CO₂Me | CF₃ |
| 82 | H | OCF₂CF₂O | | H | CH₂N(C₆H₁₁)CO₂Et | CF₃ |
| 83 | H | OCF₂CF₂O | | H | CH₂N(C₆H₁₁)CO₂Et | CHF₂ |
| 84 | H | OCFHCF₂O | | H | H | CF₃ |
| 85 | H | O(CClF)₂O | | H | H | CF₃ |
| 86 | H | O(CClF)₂O | | H | CH₂OEt | CF₃ |
| 87 | H | O(CClF)₂O | | H | CH₂N(Me)CO₂Et | CF₃ |
| 88 | H | O(CClF)₂O | | H | CH₂CN | CF₃ |
| 89 | H | O(CH₂)₂O | | H | CH₂OEt | CF₃ |
| 90 | Cl | H | SO₂CF₃ | H | H | CF₃ |
| 91 | Cl | H | SO₂CF₃ | H | H | CHF₂ |
| 92 | Br | H | CF₃ | H | CH₂COtBu | CF₃ |
| 93 | Br | H | CF₃ | H | CH₂OEt | CF₃ |
| 94 | Br | H | CF₃ | H | CH₂CO₂Bu | CF₃ |
| 95 | Br | H | CF₃ | H | CH₂N(Me)CO₂Me | CF₃ |
| 96 | Br | H | CF₃ | H | CH₂CH=CH₂ | CF₃ |
| 97 | Br | H | CF₃ | H | H | CF₃ |
| 98 | Br | H | CF₃ | H | CH₂N(iPr)CO₂Et | CF₃ |
| 99 | Br | H | CF₃ | H | CH₂N(C₆H₁₁)CO₂Et | CF₃ |
| 100 | Br | H | SO₂Me | H | H | CF₃ |
| 101 | Br | H | SO₂CF₂ | H | H | CF₃ |
| 102 | CF₃ | H | Cl | H | H | CF₃ |
| 103 | CF₃ | H | Cl | H | CH₂CN | CF₃ |
| 104 | CF₃ | H | Cl | H | CH₂COPh | CF₃ |
| 105 | CF₃ | H | Cl | H | CH₂OEt | CF₃ |
| 106 | CF₃ | H | Cl | H | CH₂N(Me)CO₂Me | CF₃ |
| 107 | CF₃ | H | Cl | H | CH₂N(Me)CO₂Et | CF₃ |
| 108 | CF₃ | H | Cl | H | CH₂N(tBu)CO₂Et | CF₃ |
| 109 | CF₃ | H | Cl | H | CH₂N(Bu)CO₂Et | CF₃ |
| 110 | CF₃ | H | Cl | H | CH₂N(Et)CO₂Et | CF₃ |
| 111 | CF₃ | H | Cl | H | CH₂N(C₆H₁₁)CO₂Et | CF₃ |
| 112 | CF₃ | H | Br | H | H | CF₃ |
| 113 | CF₃ | H | Br | H | H | CHF₂ |
| 114 | CF₃ | H | Br | H | CH₂CN | CF₃ |
| 115 | CF₃ | H | Br | H | CH₂N(Me)SO₂Me | CF₃ |
| 116 | CF₃ | H | Br | H | CH₂OPr | CF₃ |
| 117 | CF₃ | H | Br | H | CH₂N(Me)CO₂Me | CF₃ |
| 118 | CF₃ | H | Br | H | CH₂N(Pr)CO₂Et | CF₃ |
| 119 | CF₃ | H | Br | H | CH₂N(Et)CO₂Et | CF₃ |
| 120 | CF₃ | H | Br | H | CH₂N(C₆H₁₁)CO₂Et | CF₃ |
| 121 | CF₃ | H | CF₃ | H | H | CF₃ |
| 122 | CF₃ | H | CF₃ | H | H | CHF₂ |
| 123 | CF₃ | H | CF₃ | H | CH₂CN | CF₃ |
| 124 | CF₃ | H | CF₃ | H | CH₂N(Et)CO₂Et | CF₃ |
| 125 | CF₃ | H | CF₃ | H | CH₂N(Pr)CO₂Et | CF₃ |
| 126 | CF₃ | H | CF₃ | H | CH₂N(C₆H₁₁)CO₂Et | CF₃ |
| 127 | Br | H | SCF₃ | H | H | CF₃ |
| 128 | Br | H | SCF₃ | H | CH₂N(Pr)CO₂Et | CF₃ |
| 129 | CN | H | CF₃ | H | H | CF₃ |
| 130 | CN | H | CF₃ | H | H | CHF₂ |

-continued

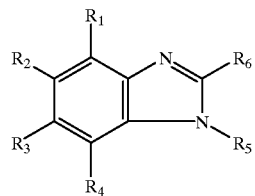

(I)

| No. | R$_1$ | R$_2$ | R$_3$ | R$_4$ | R$_5$ | R$_6$ |
|---|---|---|---|---|---|---|
| 131 | CF$_3$ | OCF$_2$—CHFCF$_3$ | H | H | SO$_2$NMe$_2$ | CF$_3$ |
| 132 | H | SCF$_3$ | | H | H | CF$_3$ |
| 133 | H | SCF$_3$ | | | CH$_2$OEt | CF$_3$ |
| 134 | H | SO$_2$Me | | | H | CF$_3$ |
| 135 | H | SO$_2$CF$_3$ | | | H | CF$_3$ |
| 136 | H | OCF$_3$ | H | H | H | CF$_3$ |
| 137 | Br | H | CF$_3$ | H | CON(CH$_3$)$_2$ | CF$_3$ |
| 138 | Br | H | CF$_3$ | H | SO$_2$-(5-chlorothien-2-yl) | CF$_3$ |
| 139 | Br | H | CF$_3$ | H | SO$_2$CH$_2$C(CH$_3$)CH$_2$ | CF$_3$ |
| 140 | Br | H | CF$_3$ | H | SO$_2$-(thien-2-yl) | CF$_3$ |
| 141 | Br | H | CF$_3$ | H | SO$_2$-(4,5-dibromothien-2-yl) | CF$_3$ |
| 142 | Br | H | CF$_3$ | H | SO$_2$-(3,5-dimethylisoxazol-4-yl) | CF$_3$ |
| 143 | Br | H | CF$_3$ | H | COOCH(CH$_3$)$_2$ | CF$_3$ |
| 144 | Br | H | CF$_3$ | H | SO$_2$—CH$_3$ | CF$_3$ |
| 145 | Br | H | CF$_3$ | H | PO(N(CH$_3$)$_2$)$_2$ | CF$_3$ |
| 146 | H | OCF$_2$O | | H | SO$_2$-(2-methoxycarbonyl-5-methylthien-3-yl) | CF$_3$ |
| 147 | H | OCF$_2$O | | H | SO$_2$-(1-methylimidazol-4-yl) | CF$_3$ |

-continued
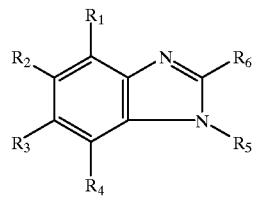
(I)
| No. | R₁ | R₂ | R₃ | R₄ | R₅ | R₆ |
|-----|----|----|----|----|----|----|
| 148 | H | OCF₂OCF₂O | | H | 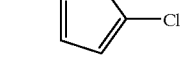 | CF₃ |
| 149 | H | OCF₂OCF₂O | | H | CON(C(CH₃)₂)₂ | CF₃ |
| 150 | H | OCF₂OCF₂O | | H | 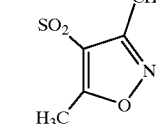 | CF₃ |
| 151 | H | OCF₂OCF₂O | | H | 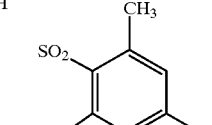 | CF₃ |
| 152 | H | OCF₂O | | H | 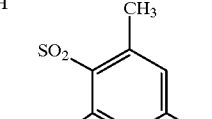 | CF₃ |
| 153 | H | OCF₂OCF₂O | | H | 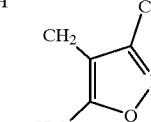 | CF₃ |
| 154 | H | OCF₂O | | H | SO₂CH₂C(CH₃)CH₂CF₃ | CF₃ |
| 155 | H | OCF₂O | | H | 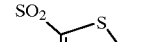 | CF₃ |
| 156 | H | OCF₂OCF₂O | | H |  | CF₃ |
| 157 | H | OCF₂O | | H |  | CF₃ |

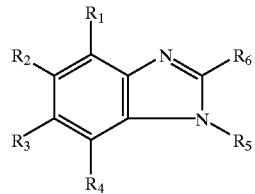

| No. | R₁ | R₂ | R₃ | R₄ | R₅ | R₆ |
|---|---|---|---|---|---|---|
| 158 | H | OCF₂OCF₂O | | H | (SO₂-pyrazole: 3-CH₃, 5-Cl, 1-CH₃) | CF₃ |
| 159 | H | OCF₂O | | H | (SO₂-thiophene-3,4-diBr... 4,5-diBr) | CF₃ |
| 160 | H | OCF₂CF₂O | | H | (SO₂-thiophene-4,5-diBr) | CF₃ |
| 161 | H | OCF₂O | | H | (SO₂-isoxazole: 3-CH₃, 5-CH₃) | CF₃ |
| 162 | H | Br | CF₃ | H | SO₂CH₃ | CF₃ |
| 163 | H | Br | CF₃ | H | (SO₂-isoxazole: 3-CH₃, 5-CH₃) | CF₃ |
| 164 | H | Br | CF₃ | H | SO₂N(CH₃)₂ | CF₃ |
| 165 | H | OCF₂CF₂O | | H | SO₂CH₂C(CH₃)CH₂ | CF₃ |
| 166 | H | OCF₂CF₂O | | H | SO₂CH₃ | CF₃ |
| 167 | H | OCF₂CF₂O | | H | PO—(N(CH₃)₂)₂ | CF₃ |
| 168 | H | Br | CF₃ | H | CO—OCH(CH₃)₂ | CF₃ |
| 169 | H | Br | CF₃ | H | CO₂N(CH₃)₂ | CF₃ |
| 170 | H | Br | CF₃ | H | PO—(N(CH₃)₂)₂ | CF₃ |

Particularly preferred compounds from the series of substituted benzimidazoles which may be particularly mentioned are:

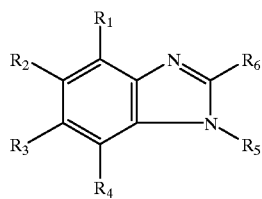

| No. | R$_1$ | R$_2$ | R$_3$ | R$_4$ | R$_5$ | R$_6$ |
|---|---|---|---|---|---|---|
| 1 | H | Br | CF$_3$ | H | H | CF$_3$ |
| 2 | H | Br | CF$_3$ | H | CH$_2$CN | CF$_3$ |
| 3 | H | CF$_3$ | Br | H | CH$_2$CN | CF$_3$ |
| 4 | H | Br | CF$_3$ | H | CH$_2$OEt | CF$_3$ |
| 5 | H | CF$_3$ | Br | H | CH$_2$OEt | CF$_3$ |
| 58 | H | Br | OCF$_3$ | H | H | CF$_3$ |
| 59 | H | Br | OCF$_3$ | H | CH$_2$CN | CF$_3$ |
| 60 | H | OCF$_3$ | Br | H | CH$_2$CN | CF$_3$ |
| 74 | H | OCF$_2$—CF$_2$O | | H | H | CF$_3$ |
| 83 | H | OCF$_2$—CF$_2$O | | H | CH$_2$N(C$_6$H$_{11}$)—CO$_2$Et | CF$_3$ |
| 92 | Br | H | CF$_3$ | H | CH$_2$COtBu | CF$_3$ |
| 95 | Br | H | CF$_3$ | H | CH$_2$N(Me)CO$_2$Me | CF$_3$ |
| 96 | Br | H | CF$_3$ | H | CH$_2$CH=CH$_2$ | CF$_3$ |
| 99 | Br | H | CF$_3$ | H | CH$_2$N(C$_6$H$_{11}$)—CO$_2$Et | CF$_3$ |
| 102 | CF$_3$ | H | Cl | H | H | CF$_3$ |
| 103 | CF$_3$ | H | Cl | H | CH$_2$CN | CF$_3$ |
| 105 | CF$_3$ | H | Cl | H | CH$_2$OEt | CF$_3$ |
| 107 | CF$_3$ | H | Cl | H | CH$_2$N(Me)CO$_2$Et | CF$_3$ |
| 108 | CF$_3$ | H | Cl | H | CH$_2$N(tBu)CO$_2$Et | CF$_3$ |
| 112 | CF$_3$ | H | Br | H | H | CF$_3$ |
| 120 | CF$_3$ | H | Br | H | CH$_2$N(C$_6$H$_{11}$)—CO$_2$Et | CF$_3$ |

Synthetic coccidiostats and polyether antibiotics which may be preferably mentioned for use in the mixtures according to the invention are:

Amprolium, in some cases in combination with folic acid antagonists

Robenidine

Toltrazuril

Monensin

Salinomycin

Maduramycin

The mixtures according to the invention are suitable, while having favourable toxicity for warm-blooded species, for controlling parasitic protazoa which occur in livestock management and livestock breeding in useful, breeding, zoo, laboratory, experimental and pet animals. They are moreover active against all or individual stages of development of the pests and against resistant and normally sensitive strains. The intention of the control of the parasitic protazoa is to reduce disease, deaths and reductions in performance (for example in the production of meat, milk, wool, hides, eggs, honey etc.) so that the use of the active compounds makes more economic and livestock management possible.

The parasitic protazoa include:

Mastigophora (Flagellata) such as, for example Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* such as, for example, Trichomonadidae, for example *Giardia lamblia, G. canis*.

Sarcomastigophora (Rhizopoda) such as Entamoebidae, for example *Entamoeba histolytica*, Hartmanellidae, for example *Acanthamoeba sp., Hartmanella sp*.

Apicomplexa (Sporozoa) such as Eimeridae, for example *Eimeria acervulina, E. adenoides, E. alabahmensis, E. anatis, E. anseris, E. arloingi, E. ashata, E. auburnensis, E. bovis. E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra,* E. spec., *E. stiedai, E. suis, E. tenella E. truncata, E. truttae, E. zuemii, Globidium spec., Isospora belli, I. canis, I. felis, I. ohioensis, I. rivolta,* I. spec., *I. suis,* Cystisospora spec., Cryptosporidium spec. such as Toxoplasmadidae, for example *Toxoplasma gondii*, such as Sarcocystidae, for example *Sarcocystis bovicanis, S. bovihominis, S. ovicanis, S. ovifelis,* S. spec., *S. suihominis* such as Leucozoidae, for example *Leucozytozoon simondi*, such as plasmodiidae, for example plasmodium berghei, *P. falciparum, P. malariae, P. ovale, P. vivax,* P. spec., such as Piroplasmea, for example *Babesia argentina, B. bovis, B. canis,* B. spec. *Theileria parva,* Theileria spec., such as Adeleina, for example *Hepatozoon canis,* H. spec.

The useful and breeding livestock include mammals such as, for example, cattle, horses, sheep, pigs, goats, camels, water buffalo, donkeys, rabbits, fallow deer, reindeer, fur-bearing livestock such as, for example, mink, chinchilla, raccoon, birds such as, for example, chickens, geese, turkeys, ducks, pigeons, bird species for keeping at home and in zoos.

Laboratory and experimental animals include mice, rats, guinea pigs, golden hamsters, dogs and cats.

Pet animals include dogs and cats.

Both prophylactic and therapeutic use is possible.

The active compounds are used directly or in the form of suitable preparations, enterally, parenterally, dermally, nasally.

Enteral use of the active compounds takes place, for example, orally in the form of powders, suppositories, tablets, capsules, pastes, drinks, granules, drenches, boli, medicated feed or drinking water. Dermal use takes place, for example, in the form of dipping, spraying, bathing, washing, pouring on and spotting on, and dusting. Parenteral use takes place, for example, in the form of injection (intramuscular, subcutaneous, intravenous, intraperitoneal) or by implants.

Suitable preparations are:

Solutions such as injection solutions, oral solutions, concentrates for oral administration after dilution, solutions for use on the skin or in body cavities, pour-on formulations, gels;

Emulsions and suspension for oral or dermal use and for injection; semisolid preparations;

Formulations in which the active compound is incorporated in an ointment base or in an oil-in-water or water-in-oil emulsion base;

Solid preparations such as powders, premixes or concentrates, granules, pellets, tablets. boli, capsules; aerosols and inhalations, shaped articles containing active compound.

Injection solutions are administered intravenously, intramuscularly and subcutaneously.

Injection solutions are prepared by dissolving the active compound in a suitable solvent and possibly adding additives such as solubilizers, acids, bases, buffer salts, antioxidants, preservatives. The solutions are sterilized by filtration and bottled.

Solvents which may be mentioned are, physiologically tolerated solvents such as water, alcohols such as ethanol, butanol, benzylalcohol, glycerol, hydrocarbons, propylene glycol, polyethylene glycol, N-methylpyrrolidone, and mixtures thereof.

The active compounds can, where appropriate, also be dissolved in physiologically tolerated vegetable or synthetic oils which are suitable for injection.

Solubilizers which may be mentioned are: solvents which promote dissolution of the active compound in the main solvent or prevent its precipitation. Examples are polyvinylpyrrolidone, polyethoxylated castor oil, polyethoxylated sorbitan esters.

Preservatives are: benzyl alcohol, trichlorobutanol, p-hydroxybenzoic esters, n-butanol.

Oral solutions are used directly. Concentrates are used orally after previous dilution to their use concentration. Oral solutions and concentrates are prepared, as described above for injection solutions, it being possible to dispense with sterile operation.

Solutions for use on the skin are spotted on, painted on, rubbed in, applied by spraying or jetting. or applied by dipping, bathing or washing. These solutions are prepared as described above for the injection solutions.

It may be advantageous to add thickeners during preparation. Thickeners are: inorganic thickeners such as bentonites, colloidal silica, aluminium monostearate, organic thickeners such as cellulose derivatives polyvinyl alcohols and their copolymers, acrylates and metacrylates.

Gels are introduced onto the applied or painted on or into body cavities. Gels are prepared by adding sufficient thickeners to solutions, which have been prepared as described for the injection solutions, to result in a clear composition with an ointment-like consistency. The thickeners used are the thickeners indicated hereinbefore.

Pour-on formulations are poured onto or sprayed onto limited areas of the skin, in which case the active compound either penetrates through the skin and acts systemically or is dispersed on the surface of the body.

Pour-on formulations are prepared by dissolving, suspending or emulsifying the active compound in suitable skin-compatible solvents or solvent mixtures. Where appropriate, other auxiliaries such as colourants, absorption-promoting substances, antioxidants, sunscreen agents, adherents are added.

Solvents which may be mentioned are: water, alkanols, glycols, polyethylene glycols, polypropylene glycols, glycerol, aromatic alcohols such as benzyl alcohol, phenyl ethanol, phenoxy ethanol, esters such as ethyl acetate, butyl acetate, benzylbenzoate, ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone, 2-dimethyl4-oxy-methylene-1,3-dioxolane.

Colourants are all colourants approved for use on livestock, and can be dissolved or suspended.

Absorption-promoting substances are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylated hydroxytoluene, butylated hydroxyanisole, tocopherol.

Sunscreen agents are, for example, substances from the class of benzophenones or novantisolic acid.

Adherents are, for example, cellulose derivatives, starch derivatives, polyacrylates, natural polymers such as alginates, gelatin.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing the latter with the assistance of suitable emulsifiers and, where appropriate, other auxiliaries such as colourants, absorption-promoting substances, preservatives, antioxidants, sunscreen agents, viscosity-increasing substances, with a solvent of the other phase.

The following may be mentioned as hydrophobic phase (oils): paraffin oils, silicone oils, natural vegetable oils such as sesame oil, almond oil, castor oil, synthetic triglycerides such as caprylic/capric acid biglyceride, triglyceride e with vegetable fatty acids of chain length $C_{8-12}$ or other specially selected natural fatty acids, partial glyceride mixtures of saturated or unsaturated, possibly also hydroxyl group-containing fatty acids, mono- and diglycerides of $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, 5 including fatty alcohols such as isotridecyl alcohol, 2-octyldodecanol, cetylstearyl alcohol, oleyl alcohol.

Fatty acids such as, for example, oleic acid and mixtures thereof.

The following may be mentioned as hydrophilic phase:

Water, alcohols such as, for example, propylene glycol, glycerol, sorbitol and mixtures thereof.

Emulsifiers which may be mentioned are:

nonionic surfactants, for example polyethoxylated castor oil, polyethoxylated sorbitan monooleate, sorbitan monostearate, glycerol monostearate, polyoxyethyl stearate, alkylphenol polyglycol ether;

ampholytic surfactants such as di-Na-N-lauryl-β-iminodipropionate or lecithin;

anionic surfactants, such as Na-lauryl sulphate, fatty alcohol ether sulphates, mono/dialkylpolyglycol ether orthophosphoric ester monoethanolamine salt; cationic surfactants such as cetyltrimethylammonium chloride.

Further auxiliaries which may be mentioned are:

Viscosity-increasing and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixTures of the substances mentioned.

Suspensions can be used orally, dermally or as injection. They are prepared by suspending the active compound in a liquid vehicle, where appropriate with the addition of further auxiliaries such as wetting agents, colourants, absorption-promoting substances, preservatives. antioxidants, sunscreen agents.

Liquid vehicles which may be mentioned are all homogeneous solvents and solvent mixtures.

Wetting agents (dispersants) which may be mentioned are the surfactants indicated hereinbefore.

Further auxiliaries which may be mentioned are those indicated hereinbefore. Semisolid preparations can be administered orally or dermally. They differ from the suspensions and emulsions described above only by their higher viscosity.

To prepare solid preparations, the active compound is mixed with suitable excipients, where appropriate with the addition of auxiliaries, and converted into the desired shape.

Excipients which may be mentioned are all physiologically tolerated solid inert substances. Used as such are inorganic and organic substances. Inorganic substances are, for example, sodium chloride, carbonates such as calcium carbonate, bicarbonates, aluminium oxides, silicas, aluminas, precipitated or colloidal silicon dioxide, phosphates.

Organic substances are, for example, sugars, cellulose, foodstuffs and feedstuffs, such as milk powder, animal meals, cereals meals and coarse meals, starches.

Auxiliaries are preservatives, antioxidants, colourants. which have already been listed hereinbefore.

Further suitable auxiliaries are lubricants and glidants, such as, for example, magnesium stearate, stearic acid, talc, bentonites, disintegration-promoting substances such as starch or crosslinked polyvinylpyrrolidone, binders such as, for example, starch, gelatine or linear polyvinylpyrrolidone, and dry binders such as microcrystalline cellulose.

The active compounds may also be present in the preparations mixed with synergists or with other active compounds.

Preparations ready for use contain the active compounds in concentrations of 10 ppm to 20 per cent by weight, preferably from 0.1 to 10 per cent by weight.

The benzimidazoles of the formula (I) are in this case present in the following ratio by weight to the synthetic coccidiostats or polyether antibiotics: 1 to 0.1–10, preferably 1 to 1–10.

Preparations which are diluted before use contain the active compounds in concentrations of 0.5 to 90 per cent by weight, preferably from 1 to 50 per cent by weight.

It has in general proved advantageous to administer amounts of about 0.5 to about 50 mg, preferably 1 to 20 mg, of active compounds per kg of bodyweight per day to achieve effective results.

The active compounds can also be administered to the livestock together with the feed or drinking water.

Feedstuffs and foodstuffs contain 0.01 to 250 ppm, preferably 0.5 to 100 ppm, of the active compound in combination With a suitable edible material.

Such a feedstuff and foodstuff can be used both for curative purposes and for prophylactic purposes.

Such a feedstuff or foodstuff is prepared by mixing a concentrate or a premix which contains 0.5 to 30%, preferably 1 to 20% by weight, of an active substance mixed with an edible organic or inorganic vehicle, with customary feedstuffs. Edible vehicles are, for example, maize meal or maize and soya bean meal or mineral salts, which preferably contain a small amount of an edible dust-preventing oil, for example corn oil or soya oil. The premix obtained in this way can then be added to the complete foodstuff before it is fed to the livestock.

The use for coccidiosis may be mentioned by way of example:

For the cure and prophylaxis, for example, of coccidiosis in poultry, in particular in chickens, ducks, geese and turkeys, 0.1 to 100 ppm, preferably 0.5 to 100 ppm, of an active compound are mixed with a suitable edible material, for example a nutritious feedstuff If required, these amounts can be increased, especially if the active compound is well tolerated by the recipient. Administration via the drinking water can take place correspondingly.

For the treatment of single animals, for example in the case of treatment of coccidiosis in mammals or of toxoplasmosis, preferably amounts of active compound of 0.5 to 100 mg/kg of bodyweight are administered each day in order to achieve the desired results. It may, nevertheless, be necessary on occasions to deviate from the stated amounts, in particular as a function of the bodyweight of an experimental animal or of the nature of the method of administration, but also because of the animal genus and its individual reaction to the active compound or the type of formulation and the time or interval over which administration takes place. Thus, it may suffice in certain cases to make do with less than the abovementioned minimum amount, whereas in other cases the stated upper limit must be exceeded. On administration of larger amounts, it may be expedient to divide these into several individual administrations over the course of the day.

The efficacy of the mixtures according to the invention can be demonstrated, for example, in cage tests with the following test design, in which the livestock are treated with the particular individual components and with the mixtures of the individual components.

Cage Test on Coccidiosis/chicks

Male chicken chicks (for example LSL Brinkschulte/Senden) which have been reared coccidia-free and are 8 to 12 days old receive the compounds according to the invention (test substances) in the concentration stated in ppm with the feed from 3 days before (day-3) the infection (=a.i.) to 8 (9) days after the infection (=p.i.). Three birds are kept in each cage. One or more such groups are used per dosage. The infection takes place using a tube direct into the crop with about 50,000 sporulated oocysts of *Eimeria acervulina* and with in each case about 20,000 sporulated oocysts of *E. maxima* and *E. tenella*. Highly virulent strains of these are used. The exact infection dose is adjusted so that, where possible, one in three untreated experimentally infected chicks dies from the infection. The following criteria are taken into account for assessing the efficacy: weight gain from start of test to end of test, mortality rate from the infection, macroscopic assessment of the faeces with regard to diarrhoea and excretion of blood on days 5 and 7 p.i. (score 0 to 6), macroscopic assessment of the intestinal mucosa, especially of the caeca (score 0 to 6) and excretion of oocysts, and the proportion (in %) of oocysts sporulating within 24 hours. The number of oocysts in the faeces was determined using a McMaster counting chamber (see Engelbrecht and coworkers "Parasitologische Arbeitsmethoden in Medizin und Veterinärmedizin, Akademie-Verlag, Berlin (1965)). The individual findings are related to the untreated uninfected control groups, and a total score is calculated (cf A. Haberkorn (1986) pages 263 to 270 in Research in Avian Coccidiosis ed. L. R. McDougald, L. P. Joyner, P. L. Long Proceedings of the Georgia Coccidiosis Conference Nov., 18.–20. 1985 Athens/Georgia U.S.A.).

A feed containing active compound is prepared in such a way that the required amount of active compound is thoroughly mixed with an animal feed which is balanced in nutrient terms, for example with the chick feed indicated below.

If a concentrate or a premix is to be prepared and is finally diluted to be in the feed to the figures mentioned in the test, in general about 1 to 30% preferably about 10 to 20% by weight of active compound are mixed with an edible organic or inorganic vehicle, for example maize and soya meal or mineral salts, which contain a small amount of an edible anti-dusting oil, for example corn oil or soya bean oil. The premix obtained in this way can then be added to the complete poultry feed before administration.

An example of a suitable composition for use of the substances according to the invention in poultry feed is the following.

52.00% coarse cereal feed meal, in particular: 40% maize, 12% wheat
17.00% extr. coarse soya meal
5.00% maize gluten feed
5.00% wheat feed meal
3.00% fish meal
3.00% mineral mixture
3.00% alfalfa meal
2.50% vitamin premix
2.00% wheatgerms, crushed
2.00% soya oil
2.00% meat and bone meal
1.50% whey powder
1.00% molasses
<u>1.00% brewers' yeast, bound to brewers' grains</u>
100.00%

Such a feed contains 18% crude protein, 5% crude fibre, 1% Ca. 0.7% P and, per kg, 1.200 I.U. of vitamin A, 1,200 I.U. of vitamin $D_3$. 10 mg of vitamin E, 20 mg of zinc bacitracin.

Test results with combinations according to the invention are listed by way of example in the following tables. The synergistic activity of the combinations by comparison with the individual components is particularly evident from a reduction in oocyst excretion, but also in respect of the necropsy findings, weight gain and better tolerability.

In the following tables, the meanings in the "treatment" column are:

n.inf.contr.=non-infected control group inf.contr.=infected control group amprol comb.=amprolium combined with sulphaquinoxaline and ethopabate 1=benzimidazole ex. No.

In the "ppm" column, the concentration of active compound used in the feed is stated in ppm.

In the "mortality" column, the percentage of birds which die is indicated under %, and the number of birds which died/birds used in the test is indicated under n.

In the "weight % of not inf.control" column, the ratio of the weight of the treated birds to the weight of the uninfected control group is indicated.

In the "dropping scores", "lesion score" and "oocyst control" columns, individual data on the effect are given.

In the "% efficay" column, the overall evaluation is scored; 0% means no effect 100% means complete effect.

TABLE 1

Experimental infection of chicks with *Eimeria acervulina*, *E. maxima* and *E. tenella*.

| Treatment | ppm | mortality % | n | weight % of not inf. control | dropping scores | lesion score | oocyst in % of inf. control ac. | max. | ten. | tot. | % efficay tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 50 | 3/6 | 46 | 6 | 6 | 100 915* | 100 55* | 100 1520* | 100 2490* | 0 |
| amprol. comb. | 50 | 0 | 0/3 | 71 | | 0.7 | 63 | 36 | 46 | 52 | 36 |
|  | 75 | 0 | 0/3 | 75 | | 0 | 100 | 36 | 100 | 78 | 42 |
| 1 | 5 | 0 | 0/3 | 80 | 4–6 | 4 | 15 | 100 | 14 | 43 | 39 |
| amprol. comb. + 1 | 50 + 5 | 0 | 0/3 | 89 | 0 | 0 | 1.5 | 2 | 1 | 1.5 | 82 |
|  | 75 + 5 | 0 | 0/3 | 95 | 0 | 0.7 | 0.26 | 0 | 0.32 | 0.29 | 98 |

\* = × 1000

TABLE 2

| Treatment | ppm | mortality % | n | weight % of not inf. control | dropping scores | lesion score | oocyst in % of inf. control ac. | max. | ten. | tot. | % efficay tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0/6 | 61 | | 6 | 100 3810* | 100 380* | 100 2980* | 100 7270* | 0 |
| monensin | 25 | 0 | 0/3 | 44 | | 6 | 44 | 100 | 100 | 81 | 7 |
|  | 50 | 0 | 0/3 | 88 | | 6 | 13 | 33 | 19 | 22 | 43 |
| 1 | 2.5 | 33 | 1/3 | 83 | 6 | 6 | 14 | 38 | 41 | 31 | 35 |
|  | 5 | 0 | 0/3 | 76 | 6 | 5.7 | 0.6 | 3 | 3 | 2.1 | 69 |
|  | 10 | 33 | 1/3# | 100 | 0–2 | 3.5 | 0 | 0 | 0 | 0 | 92 |
| monen- | 25 | 0 | 0/3 | 66 | 6 | 6 | 13 | 29 | 24 | 22 | 32 |

TABLE 2-continued

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| sin + 1 | 2.55 | | | | | | | | | | |
| | 25 + 5 | 0 | 0/3 | 102 | 0–2 | 4.3 | <0.1 | <0.1 | 0.1 | 0.1 | 92 |
| | 25 + 10 | 0 | 0/3 | 102 | 0–2 | 0.7 | 0 | 0 | <0.1 | <0.1 | 98 |
| | 50 + 2.5 | 0 | 0/3 | 97 | 1 | 0.3 | <0.1 | <0.1 | <0.1 | <0.1 | 96 |

\* = × 1000
\# = because of toxicity

TABLE 3

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 83 | 5/6 | 64 | 6 | 6 | 100 1420* | 100 220* | 100 3560* | 100 5200* | 0 |
| robenidine | 16.5 | 0 | 0/3 | 95 | 1 | 5 | 38 | 9 | 23 | 23 | 60 |
| 1 | 5 | 67 | 2/3 | 87 | 6 | 6 | 11 | 15 | 11 | 12 | 40 |
| | 10 | 33 | 1/3# | 83 | 6 | 6 | 0.8 | 0.9 | 0.6 | 0.8 | 71 |
| robenidine + 1 | 16.5 + 5 | 0 | 0/3 | 114 | 0 | 1.3 | 1.2 | 4 | 2 | 9 | 88 |
| | 16.5 + 10 | 33 | 1/3# | 96 | 0 | 4 | 0.01 | 0 | 0 | <0.01 | 94 |

\* = × 1000
\# = because of toxicity

TABLE 4

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 83 | 5/6 | 64 | 6 | 6 | 100 1430* | 100 220* | 100 3560* | 100 5200* | 0 |
| toltrazuril | 10 | 0 | 0/3 | 84 | 3 | 6 | 3 | 4 | 1 | 3 | 68 |
| | 15 | 0 | 0/3 | 106 | 5 | 3.3 | 0.6 | 0 | 0.4 | 0.3 | 88 |
| 1 | 5 | 67 | 2/3 | 87 | 6 | 6 | 11 | 15 | 11 | 12 | 40 |
| | 10 | 33 | 1/3# | 83 | 6 | 6 | 0.8 | 0.9 | 0.6 | 0.8 | 71 |
| toltrazuril + 1 | 10 + 5 | 0 | 0/3 | 76 | 6 | 6 | 0.7 | 2 | 0.6 | 1.1 | 72 |
| | 15 + 10 | 0 | 0/3 | 94 | 0 | 4.3 | 0 | 0 | 0 | 0 | 98 |

\* = × 1000
\# = because of poisoning

TABLE 5

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0.6 | 62 | 6 | 6 | 100 | 100 | 100 | 100 | 0 |
|  |  |  |  |  |  |  | 1260* | 1650* | 1640* | 3050* |  |
| monensin | 25 | 0 | 0/3 | 72 | 4 | 5.3 | 86 | >100 | >100 | 95 | 0 |
|  | 50 | 0 | 0/3 | 78 | 6 | 6 | 35 | 93 | 38 | 55 | 30 |
|  | 100 | 0 | 0/3 | 92 | 0 | 2.7 | 11 | 20 7 | 20 | 13 | 69 |
| 74 | 5 | 0 | 0/3 | 59 | 6 | 6 | >100 | 40 | >100 | 80 | 4.3 |
|  | 10 | 33 | 1/3# | 80 | 0 | 4.5 | 0.7 | 3 | 2 | 1.9 | 75 |
| Monensin + 74 | 25 + 5 | 0 | 0/3 | 83 | 0 | 5.3 | 8 | 9 | 15 | 11 | 58 |
|  | 25 + 10 | 0 | 0/3 | 80 | 4 | 4.3 | 1 | 0 | 0.9 | 0.6 | 69 |
|  | 50 + 5 | 0 | 0/3 | 90 | 0 | 2.3 | 0.08 | 0 | 0.13 | 0.07 | 98 |
|  | 50 + 10 | 33 | 1/3# | 98 | 0 | 0.5 | 0.7 | 0 | 0.05 | 0.25 | 100 |
|  | 100 + 5 | 0 | 0/3 | 89 | 0 | 1.3 | 1 | 0.7 | 4 | 1.9 | 85 |
|  | 100 + 5 | 0 | 0/3 | 87 | 0 | 0.7 | 0 | 0 | 0.02 | 0.01 | 87 |

* = × 1000
# = because of poisoning

TABLE 6

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0/6 | 59 | 6 | 6 | 100 | 100 | 100 | 100 | 0 |
|  |  |  |  |  |  |  | 2760* | 200* | 1820* | 4780* |  |
| halofuginone | 1 | 0 | 0/3 | 67 | 2 | 2 | 50 | 50 | 96 | 66 | 26 |
|  | 3 | 0 | 0/3 | 72 | 0 | 0.7 | 5 | 4 | 19 | 9 | 70 |
| 74 | 5 | 0 | 0/3 | 38 | 6 | 6 | 84 | 100 | 45 | 76 | 4 |
|  | 10 | 33 | 1/3 | 48 | 6 | 6 | 100 | 44 | 44 | 63 | 7 |
| halofuginone 74 | 1 + 10 | 0 | 0/3 | 55 | 0 | 0.7 | 2.5 | 60 | 13 | 7.2 | 53 |
|  | 3 + 5 | 0 | 0/3 | 76 | 0 | 0 | 3 | 0 | 5 | 2.7 | 85 |

* = × 1000

TABLE 7

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 33 | 2/6 | 62 | 6 | 6 | 100<br>645* | 100<br>115* | 100<br>865* | 100<br>1625* | 0 |
| salinomycin | 15 | 0 | 0/3 | 85 | 6 | 6 | 81 | 87 | 58 | 75 | 16 |
|  | 30 | 0 | 0/3 | 100 | 3–5 | 2.3 | 9 | 0 | 22 | 10 | 74 |
|  | 40 | 0 | 0/3 | 112 | 0 | 0 | 2.5 | 5 | 1.7 | 3 | 90 |
| 60 | 10 | 0 | 0/3 | 65 | 6 | 6 | 59 | 70 | 53 | 61 | 5 |
|  | 12.5 | 0 | 0/3 | 86 | 6 | 6 | 71 | 100 | 65 | 79 | 16 |
|  | 15 | 0 | 0/3 | 85 | 6 | 6 | 62 | 100 | 72 | 78 | 16 |
|  | 20 | 0 | 0/3 | 84 | 4–6 | 2.3 | 31 | 87 | 40 | 53 | 32 |
| salinomycin + 60 | 15 + 10 | 0 | 0/3 | 100 | 6 | 2.3 | 28 | 70 | 53 | 50 | 37 |
|  | 15 + 12.5 | 0 | 0/3 | 100 | 0 | 0.3 | 0.09 | 0.5 | 0.2 | 0.27 | 100 |
|  | 30 + 10 | 0 | 0/3 | 98 | 0 | 0.3 | 0 | 0 | 0 | 0 | 100 |
|  | 30 + 12.5 | 0 | 0/3 | 96 | 0 | 0 | 0 | 0.2 | 0 | 0.07 | 100 |
|  | 30 + 15 | 0 | 0/3 | 103 | 1 | 1 | 0 | 0 | 0 | 0 | 96 |
|  | 30 + 20 | 0 | 0/3 | 101 | 0 | 0.7 | 0 | 0 | 0 | 0 | 98 |
|  | 40 + 10 | 0 | 0/3 | 100 | 0 | 0 | 0.03 | 0 | 0.1 | 0.03 | 100 |
|  | 40 + 12.5 | 0 | 0/3 | 94 | 2 | 0.7 | 0 | 0 | 0 | 0 | 95 |
|  | 40 + 20 | 0 | 0/3 | 97 | 0 | 0 | 0 | 0 | 0 | 0 | 100 |

* = × 1000

TABLE 8

| Treatment | ppm | mortality % | mortality n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| contr. inf. | 0 | 17 | 1/6 | 61 | 6 | 6 | 100<br>1080* | 100<br>220* | 100<br>2550* | 100<br>3850* | 0 |
| toltrazuril | 2.5 | 0 | 0/3 | 59 | 6 | 5.3 | 12 | 9 | 11 | 11 | 25 |
| 59 | 5 | 0 | 0/3 | 61 | 6 | 6 | 91 | 100 | 99 | 100 | 0 |
|  | 25 | 33 | 1/3# | 84 | 1 | 5 | 0 | 0 | 0.2 | 0.1 | 79 |
| 59 + toltrazuril | 2.5 + 2.5 | 0 | 0/3 | 69 | 6 | 5.7 | 11 | 9 | 12 | 11 | 35 |
|  | 2.5 + 25 | 0 | 0/3 | 92 | 0 | 2 | 0 | 0 | 0 | 0 | 100 |

* = × 1000
# = because of toxicity

TABLE 9

| Treatment | ppm | mortality % | n | weight % of not inf. control | dropping scores | lesion score | oocyst in % of inf. control ac. | max. | ten. | tot. | % efficacy tot. |
|---|---|---|---|---|---|---|---|---|---|---|---|
| n. inf. contr. | 0 | 0 | 0/6 | 100 | 0 | 0 | 0 | 0 | 0 | 0 | 100 |
| inf. contr. | 0 | 0 | 0/6 | 54 | 6 | 6 | 100 1570* | 100 70* | 100 1057* | 100 2697* | 0 |
| halofuginone | 1 | 33 | 1/3 | 81 | 4–6 | 6 | 41 | 100 | 49 | 63 | 24 |
|  | 3 | 0 | 0/3 | 87 | 0 | 0 | <0.1 | 0 | <0.1 | <0.1 | 91 |
| 112 | 1 | 0 | 0/3 | 41 | 6 | 6 | 100 | 57 | 91 | 83 | 0 |
|  | 5 | 0 | 0/3 | 88 | 0–2 | 6 | 0.8 | 10 | 2.4 | 4.4 | 77 |
| Halofuginone 112 | 1 + 1 | 33 | 1/3 | 88 | 6 | 6 | 12 | 100 | 17 | 43 | 30 |
|  | 3 + 1 | 0 | 0/3 | 102 | 0 | 0 | 1 | 0 | 0.7 | 0.6 | 96 |
|  | 3 + 5 | 0 | 0/3 | 83 | 0 | 1.7 | <0.1 | 0.6 | 0.2 | 0.1 | 89 |

\* = × 1000

We claim:

1. A mixture of a substituted benzimidazole of the formula

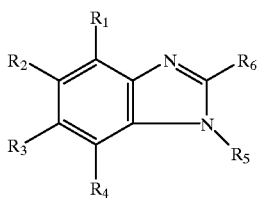

(I)

in which $R_1$, $R_2$, $R_3$ and $R_4$ each, independently of one another, represent hydrogen, halogen, represent in each case optionally substituted alkyl, alkoxy, alkylthio, alkylsulphinyl, alkylsulphonyl, represent optionally substituted fused-on dioxyalkylene, but where at least one of the substituents $R_1$, $R_2$, $R_3$ and $R_4$ is neither hydrogen nor halogen, $R_5$ represents hydrogen, represents alkyl which is substituted one or more times, identically or differently, by OH, CN, $NH_2$, alkyl, cycloalkyl, alkenyl, alkinyl, alkoxy, halogenoalkoxy, alkylthio, halogenoalkylthio, alkenoxy, alkinoxy, aminocarbonyl, optionally substituted alkylcarbonyl, optionally substituted heteroarylcarbonyl, optionally substituted alkoxycarbonyl (AlkO—CO—), optionally substituted alkoxycarbonyloxy (AlkOCOO—), aminosulphonyl ($SO_2NH_2$), optionally substituted mono- or dialkylaminosulphonyl, alkylsulphonyl, alkenylsulphonyl, hetero-arylsulphonyl, or —$SO_2NR_8R_9$, —$CONR_8R_9$ or —$P(O)(NR_8R_9)_2$, where $R_8$ and $R_9$ represent H or alkyl which is optionally substituted by one or more radicals, acylated amino (AlkCON($R_7$)— or AlkOCON($R_7$)—), where $R_7$ hydrogen, alkyl or cycloalkyl, or optionally substituted alkylsulphonylamino (AlkylSO$_2$NH—), or alkylsulphonyl-N-alkylamino (ArylSO$_2$NAlkyl—),
optionally substituted arylsulphonylamino (ArylSO$_2$, NH—) or arylsulphonyl-N-alkylamino (ArylSO$_2$NAlk—), optionally substituted dialkylamino, $R_6$ represents fluoroalkyl, with a polyether antibiotic selected from the group consisting of maduramycin, lasalocid, monensin, narasin, and salinomycin or one or more synthetic coccidiostat selected from the group consisting of 1(-(4-Amino-2-n-propyl-5-pyrimidinylmethyl)-2-picolinium chloride, 1(-(4-Amino-2-n-propyl-5-pyrimidinylmethyl)-2-picolinium chloride+sulfaquinoxaline, 1(-(4-Amino-2-n-propyl-5-pyrimidinylmethyl)-2-picolinium chloride+sulfaquinoxaline+ethopabate, 4,4-Dinitrocarbanilide+2-hydroxy-4,6-dimethylpyrimidine, 3,5-Dichloro-2,6-dimethyl-4-pyridinol, 3,5-Dichloro-2,6-dimethyl-4-pyridinol+methyl 7-benzyloxy-6-butyl-1,4-dihydro-4-oxylquinoline-3-carboxylate, Ethyl 6-n-decyloxy-7-ethoxy-4-hydroxyquinoline-3-Carboxylate, 9-(2-Chloro-6-fluorophenylmethyl)-9H-purin-6-amine, (±)-2,6-Dichloro-alpha-(4-chlorophenyl)-4-(4,5-dihydro-3,5-dioxo-1,2,4-triazin-2(3H)-yl)-benzeneacetonitrile, 1-[3-Methyl-4-(4'-trifluoromethylthiophenoxy)-phenyl]-3-methyl-1,3,5-triazine-2,4,6(1H,3H,5H)-trione, 4,4-Dinitrocarbanilide+2-hydroxy-4,6-dimethylpyrimidine, 7-Bromo-6-chloro-febrifugin, and 3,5-Dinitro-o-toluamide as a composition for controlling parasitic protozoa.

2. A process for preparing a mixture for controlling parasitic protozoa in livestock comprising admixing the benzimidazole with the polyether antibiotic or the synthetic coccidiostat as recited in claim 1.

3. A method of treating livestock to control parasitic protozoa comprising administering to the livestock an effective amount of the mixture of claim 1.

* * * * *